United States Patent
Allard et al.

(10) Patent No.: US 7,766,918 B2
(45) Date of Patent: Aug. 3, 2010

(54) SPINAL DISC REPLACEMENT SURGICAL INSTRUMENT AND METHODS FOR USE IN SPINAL DISC REPLACEMENT

(75) Inventors: Randy N. Allard, Germantown, TN (US); Loic Josse, Denens (CH); Mingyan Liu, Bourg la Reine (FR); Jeffrey Zhang, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 904 days.

(21) Appl. No.: 11/344,946

(22) Filed: Jan. 31, 2006

(65) Prior Publication Data

US 2007/0191857 A1    Aug. 16, 2007

(51) Int. Cl.
*A61B 17/56* (2006.01)
(52) U.S. Cl. .............................. 606/90; 606/79; 606/105
(58) Field of Classification Search .................. 606/90, 606/99, 105, 86 A, 79
See application file for complete search history.

(56) References Cited

U.S. PATENT DOCUMENTS

| | | | | |
|---|---|---|---|---|
| 3,486,505 | A * | 12/1969 | Morrison | 606/90 |
| 5,431,658 | A * | 7/1995 | Moskovich | 606/99 |
| 6,159,215 | A | 12/2000 | Urbahns et al. | 606/86 |
| 6,478,800 | B1 | 11/2002 | Fraser et al. | 606/99 |
| 6,520,967 | B1 | 2/2003 | Cauthen | 606/99 |
| 6,652,533 | B2 | 11/2003 | O'Neil | 606/100 |
| 6,929,647 | B2 | 8/2005 | Cohen | 606/99 |
| 7,169,152 | B2 * | 1/2007 | Foley et al. | 606/90 |
| 7,479,160 | B2 * | 1/2009 | Branch et al. | 623/17.11 |
| 7,491,204 | B2 | 2/2009 | Marnay et al. | |
| 7,547,308 | B2 * | 6/2009 | Bertagnoli et al. | 606/90 |
| 2001/0005796 | A1 | 6/2001 | Zdeblick et al. | 623/17.11 |
| 2002/0116009 | A1 * | 8/2002 | Fraser et al. | 606/99 |
| 2003/0055503 | A1 * | 3/2003 | O'Neil | 623/17.11 |
| 2003/0225416 | A1 | 12/2003 | Bonvallet et al. | 606/105 |
| 2004/0030387 | A1 * | 2/2004 | Landry et al. | 623/16.11 |
| 2004/0059318 | A1 | 3/2004 | Zhang et al. | 606/1 |
| 2004/0148028 | A1 * | 7/2004 | Ferree et al. | 623/17.11 |

(Continued)

*Primary Examiner*—Eduardo C Robert
*Assistant Examiner*—Ellen C Hammond

(57) ABSTRACT

A spinal disc replacement surgical instrument includes a first contacting member positionable along an endplate of a first vertebra and a second contacting member positionable along an endplate of second vertebra. The second contacting member is moveable relative to the first contacting member. A handle assembly is coupled to the first contacting member and the second contacting member. At least one actuating member is positioned between the first contacting member and the second contacting member. The at least one actuating member is moveable by the hand assembly from a first position, wherein the first and second contacting members include an unexpanded configuration relative to one another for insertion in the spinal cavity, to a second position providing expanded configuration relative to one another. The actuating member is configured to displace at least one of the first contacting member and the second contacting member away from each other to move the first contacting member and the second contacting member between the first position and the second position. The first contacting member has a first distal end and the second contacting member has a second distal end. The first end has a first end shape configured to conform to a shape of the first vertebra and the second end has a second end shape configured to conform to a shape of the second vertebra. The first end shape and the second end shape are different shapes.

24 Claims, 7 Drawing Sheets

U.S. PATENT DOCUMENTS

| | | |
|---|---|---|
| 2004/0176853 A1* | 9/2004 | Sennett et al. ............ 623/17.16 |
| 2004/0220567 A1 | 11/2004 | Eisermann et al. ............ 606/61 |
| 2004/0225295 A1 | 11/2004 | Zubok et al. .................. 606/90 |
| 2004/0225366 A1 | 11/2004 | Eisermann et al. ....... 623/17.15 |
| 2004/0249465 A1 | 12/2004 | Ferree ..................... 623/17.16 |
| 2005/0004672 A1* | 1/2005 | Pafford et al. ............ 623/17.11 |
| 2005/0010294 A1 | 1/2005 | Michelson ............... 623/17.11 |
| 2005/0027300 A1* | 2/2005 | Hawkins et al. ............... 606/86 |
| 2005/0038442 A1 | 2/2005 | Freeman ..................... 606/86 |
| 2005/0065606 A1 | 3/2005 | Jackson ................... 623/17.11 |
| 2005/0113842 A1* | 5/2005 | Bertagnoli et al. ............ 606/90 |
| 2005/0119665 A1 | 6/2005 | Keller ......................... 606/99 |
| 2005/0131536 A1 | 6/2005 | Eisermann et al. ....... 623/17.11 |
| 2005/0131543 A1 | 6/2005 | Benzel et al. ............. 623/17.13 |
| 2005/0177173 A1 | 8/2005 | Aebi et al. .................. 606/105 |
| 2005/0216085 A1 | 9/2005 | Michelson ............... 623/17.11 |
| 2005/0228500 A1 | 10/2005 | Kim et al. ................. 623/17.13 |
| 2006/0030856 A1* | 2/2006 | Drewry et al. ................ 606/90 |
| 2006/0085077 A1* | 4/2006 | Cook et al. .............. 623/17.15 |
| 2006/0200241 A1* | 9/2006 | Rothman et al. .......... 623/17.13 |
| 2006/0287728 A1* | 12/2006 | Mokhtar et al. ........... 623/17.14 |
| 2007/0100347 A1* | 5/2007 | Stad et al. ..................... 606/90 |
| 2007/0162040 A1* | 7/2007 | Grabowski et al. ............ 606/90 |
| 2007/0233143 A1* | 10/2007 | Josse et al. .................... 606/90 |
| 2007/0276370 A1* | 11/2007 | Altarac et al. ................. 606/61 |
| 2008/0071279 A1* | 3/2008 | Bandeira et al. .............. 606/90 |
| 2008/0132902 A1* | 6/2008 | Bertagnoli et al. ............ 606/99 |

* cited by examiner

SPINAL DISC REPLACEMENT SURGICAL INSTRUMENT AND METHODS FOR USE IN SPINAL DISC REPLACEMENT

TECHNICAL FIELD

The present invention relates generally to the field of surgery and medical implants, and more particularly, to surgical tools and methods for use in positioning an intervertebral device between vertebral members of a patient.

BACKGROUND OF THE INVENTION

The human spine is a biomechanical structure with thirty-three vertebral members, and is responsible for protecting the spinal cord, nerve roots and internal organs of the thorax and abdomen. The spine also provides structure support for the body while permitting flexibility of motion. A significant portion of the population will experience back pain at some point in their lives resulting from a spinal condition. The pain may range from general discomfort to disabling pain that immobilizes the individual. Back pain may result from a trauma to the spine, be caused by the natural aging process, or may be the result of a degenerative disease or condition.

Procedures to remedy back problems sometimes require correcting the distance between vertebral members by inserting an intervertebral device (e.g., spacer) between the members. The spacer, which is carefully positioned within the disc space and aligned relative to the vertebral members, is sized to position the vertebral members in a manner to alleviate the patient's back pain.

Further, the intervertebral device is preferably designed to facilitate insertion into a patient. That is, the shape and size of the device are designed to provide for minimal intrusion to a patient during insertion, but still be effective post-insertion to alleviate the pain and provide maximum mobility to the patient. A spinal cavity for receiving the intervertebral device must be prepared prior to inserting the device therein.

Thus, a need exists for enhanced surgical instruments and methods for positioning an intervertebral device between vertebral members of a patient, and for enhanced surgical instruments and methods for preparing a spinal cavity to receive such an intervertebral device.

SUMMARY OF THE INVENTION

The present invention provides, in an aspect, a spinal disc replacement surgical instrument which includes a first contacting member positionable along an endplate of a first vertebra. A second contacting member is positionable along an endplate of a second vertebra. The first vertebra and the second vertebra define the spinal cavity. The second contacting member is moveable relative to the first contacting member. A handle assembly is coupled to the first contacting member and the second contacting member. At least one actuating member is positioned between the first and second contacting members. The at least one actuating member is moveable by the hand assembly from a first position, wherein the first and second members include an unexpanded configuration relative to one another for insertion in the spinal cavity, to a second position providing an expanded configuration. The actuating member is configured to displace at least one of the first contacting member and the second contacting member away from each other to move the first contacting member and the second contacting member between the first position and the second position. The first contacting member has a first distal end and the second contacting member has a second distal end. The first end has a first end shape configured to conform to a shape of the first vertebra and the second end has a second end shape configured to conform to a shape of the second vertebra. The first end shape and the second end shape are different shapes.

The present invention provides, in another aspect, a spinal disc replacement surgical instrument which includes a first contacting member positionable along an endplate of a first vertebra. A second contacting member is positionable along an endplate of a second vertebra. The first vertebra and the second vertebra define a spinal cavity. The second contacting member is moveable relative to the first contacting member. The first contacting member is connected to a handle assembly by a first extending arm and the second member is connected to the handle assembly by a second extending arm. An adjustable depth regulator extends from the handle assembly toward the first member and the second member. The adjustable depth regulator is located at least partially longitudinally offset relative to at least one of the first arm and the second arm. The adjustable depth regulator includes at least one stop member positionable in contact with one of the first vertebra and the second vertebra to limit an insertion depth of the first contacting member and the second contacting member in the spinal cavity.

The present invention provides, in a further aspect, a spinal disc replacement surgical instrument which includes a first member positionable along an endplate of a first vertebra and a second member positionable along an endplate of a second vertebra. The first vertebra and the second vertebra define a spinal cavity. The second member is moveable relative to the first member. The first member and the second member are moveable between an unexpanded configuration relative to one another for insertion in the spinal cavity and an expanded configuration relative to one another. The handle assembly includes a distal end coupled to the first member and the second member. The handle assembly includes a proximal end connectable to a releaseable handle. The proximal end includes a handle assembly cavity for receiving an end of the handle and the handle assembly cavity includes an interior surface connectable to the handle. The handle assembly cavity includes an impactable head configured to receive an impact and to transfer the impact to the handle assembly and to at least one of the first contacting member and the second contacting member.

The present invention provides, in yet another aspect, a method for use in spinal disc replacement which includes positioning a first contact member of a surgical instrument along an endplate of first vertebra. A second contacting member of the surgical instrument is positioned along an endplate of a second vertebra. The first vertebra and the second vertebra define a spinal cavity. The first contacting member is coupled to the second contacting member by a handle assembly of the surgical instrument. At least one actuating member of the surgical instrument is positioned between the first contacting member and the second contacting member. The actuating member is moved from a first position, wherein the first contacting member and the second contacting member include an unexpanded configuration relative to one another for insertion in the spinal cavity, to a second position, wherein the first contacting member and the second contacting member include an expanded configuration relative to one another. The first contacting member has a first distal end and the second contacting member has a second distal end. The first distal end has a first end shape configured to conform to a shape of the first vertebra and a second end has a second end shape configured to conform to a shape of the second vertebra. The first end shape and the second end shape are different shapes.

The present invention provides, in yet a further aspect, a method for use in spinal disc replacement which includes positioning a first contacting member of a surgical instrument along an endplate of a first vertebra of a spinal cavity. A second contacting member of the surgical instrument is positioned along an endplate of the second vertebra. The first vertebra and the second vertebra define a spinal cavity. The first contacting member is connected to a handle assembly of the surgical instrument by a first extending arm and the second contacting member is connected to the handle assembly by a second extending arm. An adjustable depth regulator is extended from the handle assembly toward the first contacting member and the second contacting member such that the adjustable depth regulator is located at least partially longitudinally offset relative to at least one of the first arm and the second arm. The adjustable depth regulator is contacted with one of the first vertebra and the second vertebra to limit an insertion depth of the first contacting member and the second contacting member into the spinal cavity.

The present invention provides, in another aspect, a method for use in replacing a spinal disc which includes providing a spinal disc replacement surgical tool having a handle assembly with a distal end coupled to a first contacting member positionable along a endplate of a first vertebra defining a spinal cavity and a second contacting member positionable along an endplate of a second vertebra defining the spinal cavity. The handle assembly includes a proximal end having a handle assembly cavity connectable to a releasable handle. An impactable head in the handle assembly is impacted to cause movement of the surgical tool toward the spinal cavity.

BRIEF DESCRIPTION OF THE DRAWINGS

The subject matter, which is regarded as the invention, is particularly pointed out and distinctly claimed in the claims at the conclusion of the specification. The foregoing and other objects, features, and advantages of the invention will be apparent from the following detailed description of preferred embodiments taken in conjunction with the accompanying drawings in which:

DETAILED DESCRIPTION

In accordance with the principles of the present invention, a spinal disc replacement surgical instrument, and methods for use in implanting a prosthetic disc in a spinal cavity, are provided.

Figure 1:
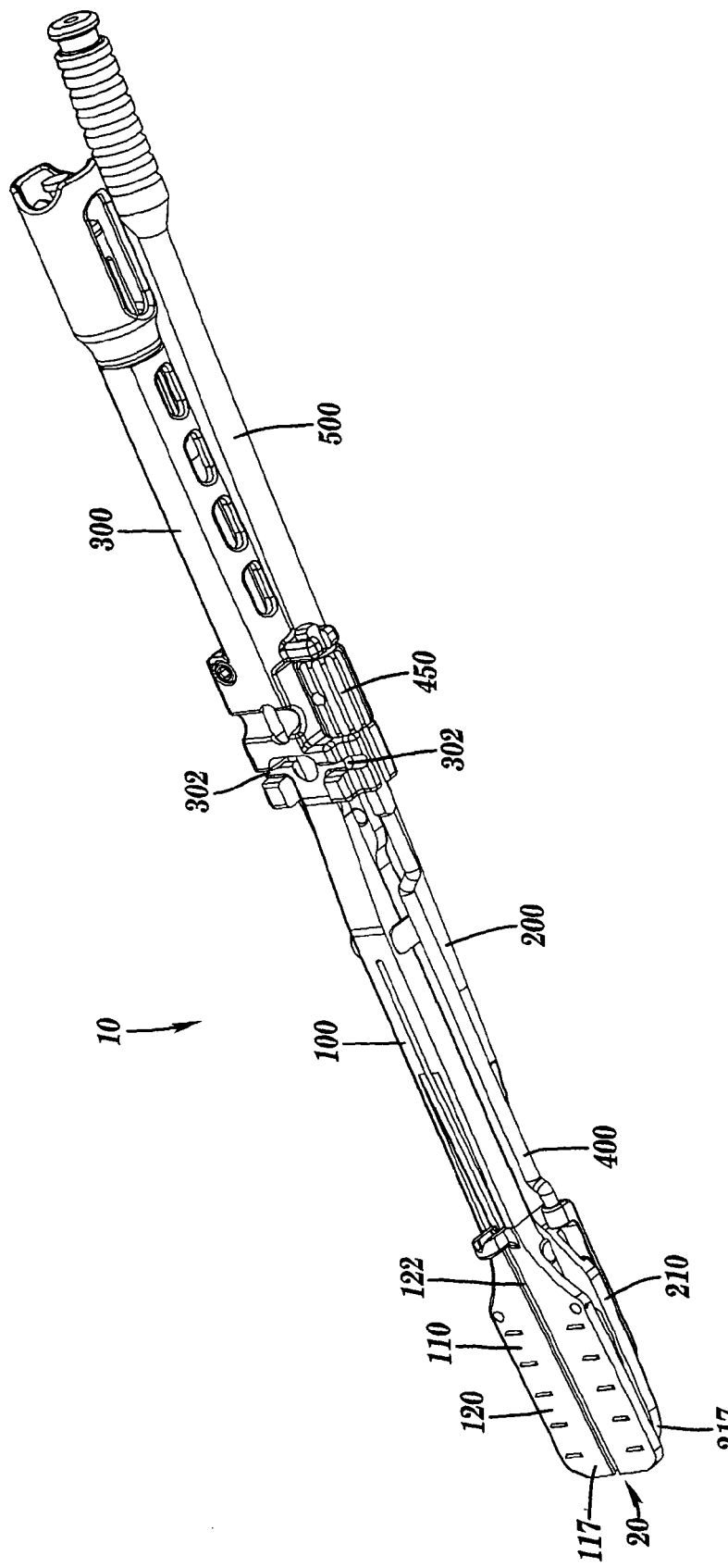
FIG. 1 is a perspective view of one embodiment of a spinal disc replacement surgical instrument with a keel cutter in a top slot of the instrument, according to an aspect of the present invention.

As depicted in FIG. 1, a surgical tool 10 includes a first arm 100, a second arm 200, and a handle assembly 300 connected to first arm 100 and second arm 200. First arm 100 and second arm 200 are hingedly and/or pivotally connected to handle assembly 300 to allow the arms to be separated from one another and moved toward one another. More specifically, first arm and second arm 200 are movable to a collapsed position (FIG. 2) such that a front end (i.e., distal end) 20 of tool 10 may be positionable in a space between adjacent vertebra (not shown) defining a spinal cavity (not shown). The arms may be remotely manipulated by a user (e.g., a surgeon) to increase a separation distance and/or angulation between endplates of adjacent vertebra defining such a spinal cavity, as depicted for example in FIG. 3. The distance between the arms may be increased (or decreased) by the manipulation of handle assembly 300 thereby adjusting a distance between the vertebra, as further described below.

Figure 5:
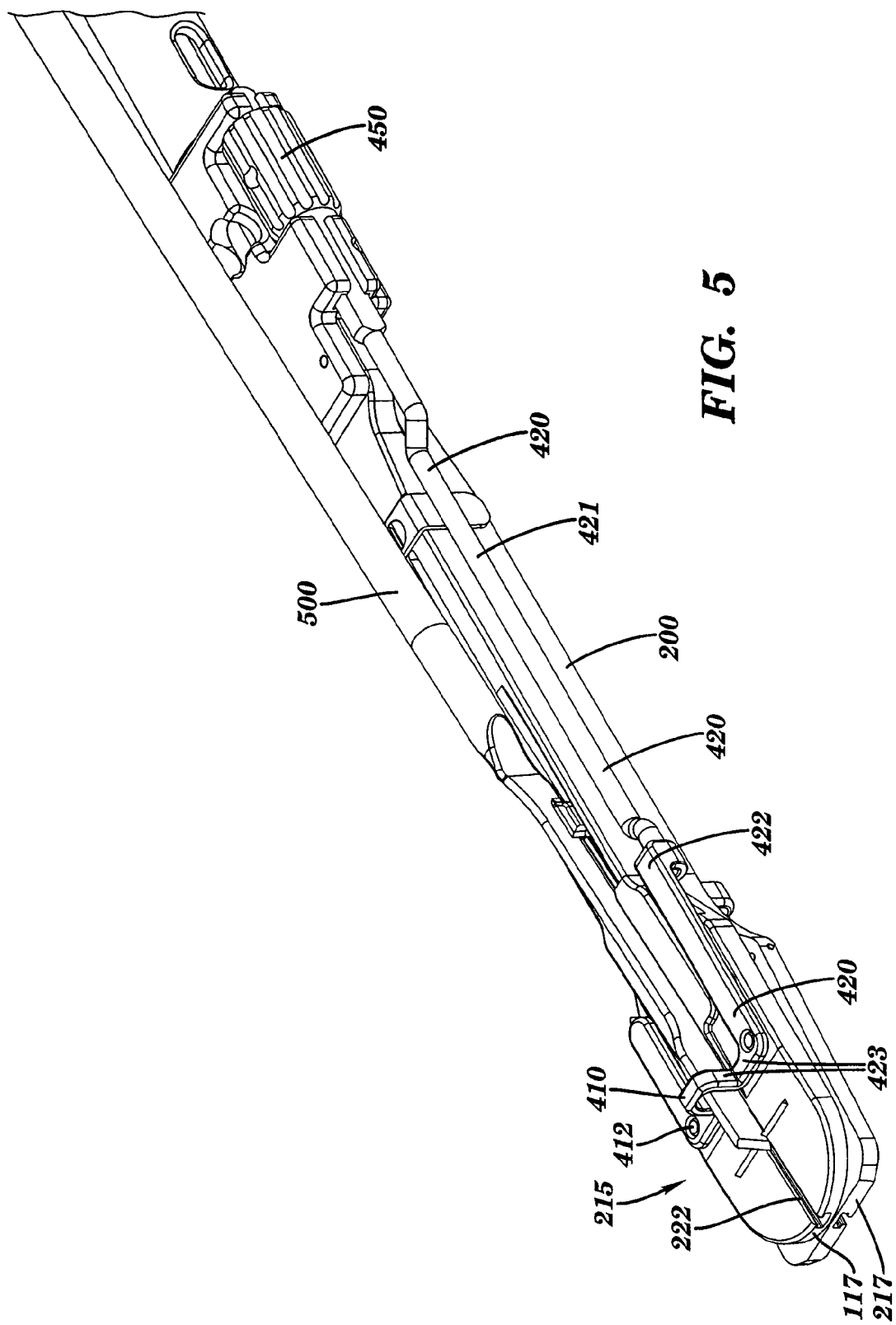
FIG. 5 is a bottom perspective view of the instrument of FIG. 1 further including a keel cutter in a bottom slot of the instrument, in accordance with an aspect of the present invention.

First arm 100 is connected to a first contacting member 110 and second arm 200 is connected a second contacting member 210. Alternatively, each arm and respective contacting member may be formed integral to one another. The members may be formed of plates having opposite faces positionable against endplates of adjacent vertebra (not shown) defining a spinal cavity (not shown) to provide a separation force to the endplates when manipulated with handle assembly 300. Other forms for contacting members 110, 210 are also contemplated, including single blades, U-shaped blades, or other suitable structure for contacting the adjacent vertebral endplate. As depicted in FIGS. 1-3 and 5, a distal end of first contacting member 110 and a distal end of second contacting member 210 may have different shapes and may extend distally (i.e., in a direction away from handle assembly 300) a different distance relative to one another. The contacting members may be tapered toward the arms at an intersection point between each arm and each contacting member. Opposite sides of the contacting members may be substantially parallel to a longitudinal axis of the contacting members and/or the arms. For example, first contacting member 110 may have a square front end 117 and second contacting member 210 may have a rounded front end 217 as best depicted in FIG. 5.

Also, the different shapes of the front ends (e.g., front ends 117 and 217) allow a user to more readily determine the correct orientation of the tool, i.e., which side (e.g., first contacting member 110) is to be used adjacent an upper vertebra and which slide (e.g., second contacting member 210) is to be used adjacent a lower vertebra. In the example depicted in the figures, a user would know from the square shape of first contacting member 110 that tool 10 is configured to be inserted such that first contacting member 110 is on a top (i.e., superior) side of the tool and is configured to abut an upper vertebra of a spinal cavity. Similarly, the user would know from the rounded or curved shape of second contacting member 210 that tool 10 is configured to be inserted such that second contacting member 210 is on a bottom (i.e., inferior) side of the tool and is configured to abut a lower vertebra of the spinal cavity. Also, the distal ends of the contacting members could be formed of any shape which conforms to the shape of a vertebra which it will abut, or come in close proximity to. For example, it may be necessary to use particular surgical instruments (e.g., tool 10) having contacting members with different shaped ends according to which vertebra in a spinal column needs to be replaced. Further, the contacting members and/or arms may be releasably connectable to each other and/or the remainder of tool 10 to allow such varying shapes and/or thicknesses of the contacting members and/or arms to be utilized.

Figure 4:
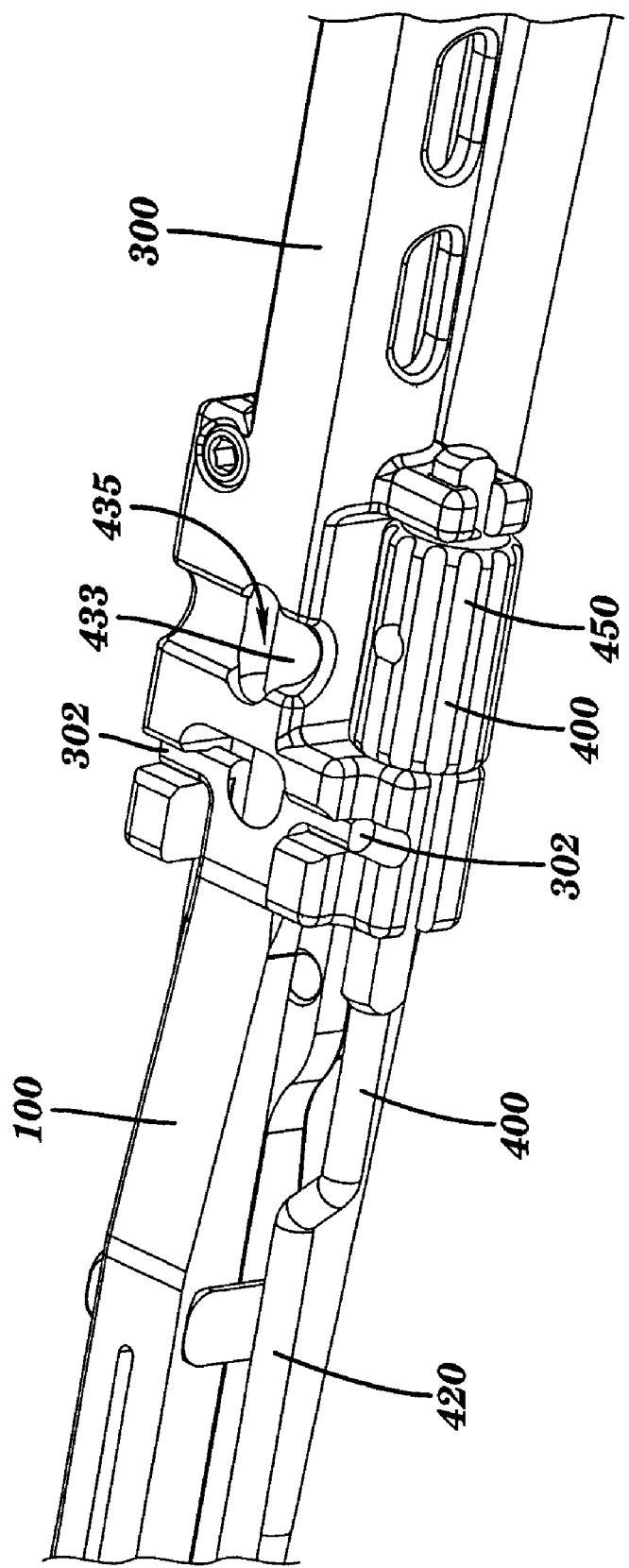
FIG. 4 is a top perspective view of a portion of the instrument of FIG. 1 showing a first extending arm, a handle assembly, and a controlling mechanism, in accordance with an aspect of the present invention.

A depth adjustment system 400 is connected to handle assembly 300 and second contacting member 210 as depicted in FIGS. 1, 4 and 5. Adjustment system 400 includes a depth regulator or stopper 410 protruding from a bottom side of a connecting member 420 movably attached to an underside 215 of second contacting member 210. Depth stopper 410 may be connected, or integral, to a connecting member 420. Depth stopper 410 is configured (e.g., shaped and dimensioned) to inhibit front end 20 of tool 10 from proceeding past a desired point into a spinal cavity. More specifically, depth stopper 410 may abut an exterior surface (i.e., a surface of a vertebra outside the spinal cavity, (not shown) of a bottom vertebra (not shown) defining a spinal cavity (not shown)) such that depth stopper 410 remains outside the spinal cavity abutting the exterior surface of the bottom vertebra defining the cavity.

Figure 2:
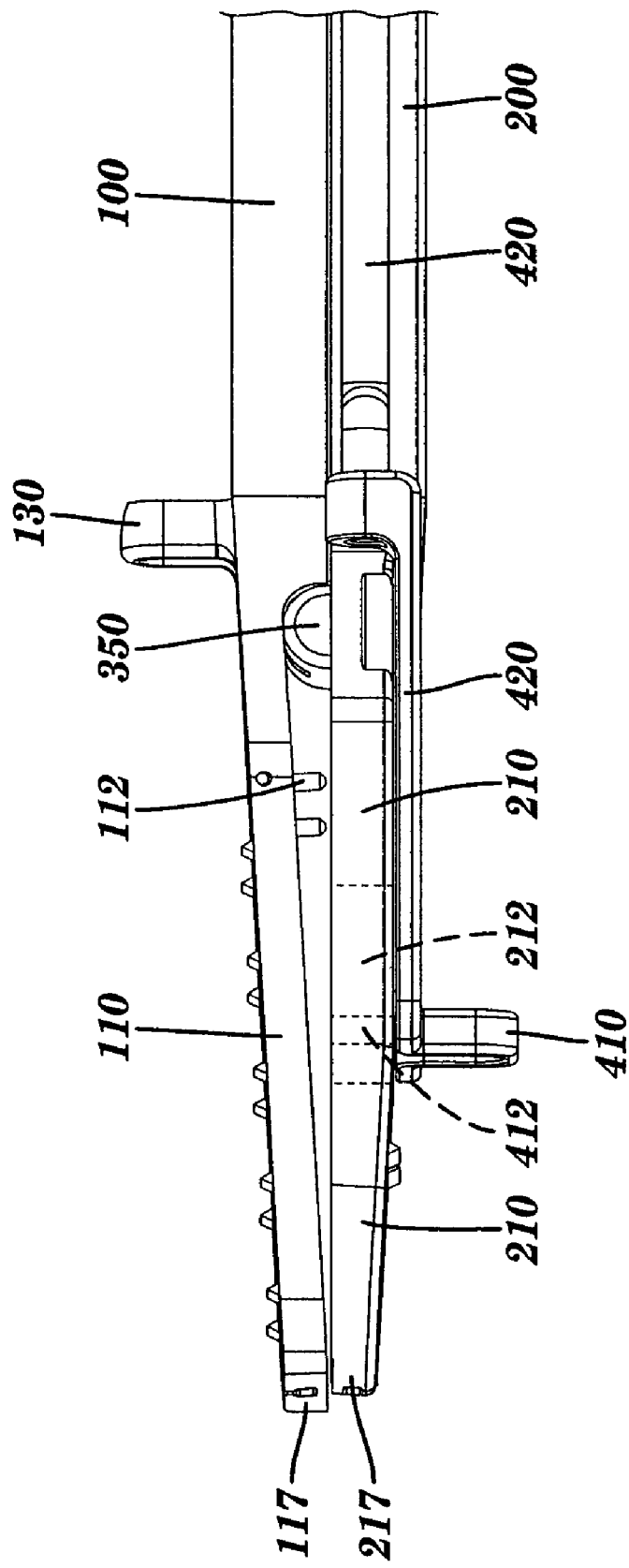
FIG. 2 is a side elevational view of a portion of the instrument of FIG. 1 showing a first contacting member and a second contacting member in an unexpanded configuration in accordance with an aspect of the present invention.

Upwardly extending portions 412 of connecting member 420 may extend through apertures 212 in second contacting member 210 as depicted in FIGS. 1, 2 and 5. Apertures 212 are elongated in a longitudinal direction relative to second contacting member 210 and tool 10 such that upwardly extending portions 412 may move in a longitudinal direction within aperture 212. Connecting member 420 connects second contacting member 210 to a controlling mechanism configured to cause the movement of connecting member 420 and depth stopper 410. Such movement allows the adjustment of the depth to which front end 20 of tool 10 may extend into a spinal cavity.

For example, such a controlling mechanism may include a rotatable knob or thumbwheel 450 having an internal thread (not shown) configured to mate with threads (not shown) on an outer surface of connecting member 420, as depicted in FIGS. 1 and 4. The rotation of thumbwheel 450 may cause connecting member 420 to move toward, or away from, rounded front end 217 of second contacting member 210. For example, the rotation of thumbwheel 450 in a clockwise direction may cause connecting member 420 to move toward rounded front end 217 until rotation is stopped at a position which corresponds to a minimum depth of the tool in a spinal cavity. Rotation of thumbwheel 450 in a counterclockwise direction may cause movement of the connecting member and the depth stopper away from rounded front end 217 to a maximum depth of tool 10 in the spinal cavity. As noted above, the movement of connecting member 420, along with depth stopper 410, controls the extent to which tool 10 (i.e., front end 20) may extend into a spinal cavity.

Thumbwheel 450 and, some or all of, the remainder of depth adjustment system 400 may be offset relative to the remainder of tool 10. For example, thumbwheel 450 may be located laterally relative to a longitudinal axis of handle assembly 300 and/or arms 100 and 200 as depicted in FIGS. 1 and 4. Connecting member 420 may also be located at least partially laterally relative to the arms (e.g., first arm 100 and second arm 200), and may be separated therefrom by a space along some or all of its length as depicted in FIGS. 1, 4, and 5. For example, connecting member 420 may be spaced from first arm 100 and second arm 200, along a length of connecting member 420 in a direction toward first contacting member 110 and second contacting member 210 from handle assembly 300 until a point of contact of connecting member 420 with one of the contacting members (e.g., second contacting member 210). As noted above, depth stopper 410 may be located on underside 215 of second contacting member 210 and located aligned with the longitudinal axis of second contacting member 210, handle assembly 300 and/or tool 10.

In the example depicted (see e.g., FIG. 5), connecting member 420 extends (i.e., curves) from a thumbwheel 450 toward arms 100, 200 to a lateral position 421 spaced from (and parallel to, along at least a portion of the length of) the arms and to a position 422 further away from the longitudinal axis of tool 10 to connect connecting member 420 to second contacting member 210 at an outer edge of second contacting member 210. The curves of connecting member 420 toward such longitudinal axis and away therefrom allows connecting member 420 to follow a contour of second arm 200 between thumbwheel 450 and second contacting member 210. Also, connecting member 420 may include a transverse portion 423 extending transversely relative to a longitudinal axis of tool 10, first contacting member 110 and second contacting member 210, first arm 100 and/or second arm 200 as depicted in FIG. 5. In an undepicted example, connecting member 420 may be connected to second contacting member 210 at one location instead of the two locations opposite depth stopper 410 depicted in FIG. 5. It will be understood by one skilled in the art that connecting member 420 may be formed of any shape such that it connects thumbwheel 450 and depth stopper 410 such that thumbwheel 450 and connecting member 420 are at least partially offset from a longitudinal axis of first arm 100 and/or second arm 200 and such that depth stopper 410 is connected to first contacting member 110 or second contacting member 210 and is located at about a longitudinal axis of tool 10, arms 100, 200, and/or first member 110 and second member 210.

The offset (e.g., lateral) location of adjustment system 400 relative to the arms and the remainder of tool 10 allows ready access to the user. For example, the location of thumbwheel 450 offset from the longitudinal axis of handle assembly 300 and/or arms 100 and 200 allows the user to easily locate thumbwheel 450 and therefore move depth stopper 410 during use. Also, the location of thumbwheel 450 and the remainder of depth adjustment system 400 at least partially offset from a longitudinal axis of tool 10 and arms 100, 200 allow the depth adjustment system 400 to avoid interfering with hinges 302 located at the intersection of the arms and handle assembly 300. The offset nature of depth adjustment system 300 therefore allows the arms to be readily moved relative to handle assembly 300 at the hinges.

A top side 120 of first contacting member 110 and first arm 100 may include a slot 122 configured to receive a keel cutter 500, as depicted in FIGS. 1 and 4. A bottom side 220 of second contacting member 210 and second arm 200 may also include a bottom slot 222 configured (e.g., shaped and dimensioned) to receive keel cutter 500 as depicted in FIG. 5. Keel cutter 500 is utilized to cut or form a keel or channel in a top and/or bottom vertebra defining a spinal cavity in which a spinal implant is to be inserted. Also, the slots on arms 100 and 200 (e.g., slot 122 and slot 222) guide the cutting of the keel by maintaining the keel aligned with a longitudinal axis of arms 100, 200 and first and second contacting members 110, 210. Depth stopper 410 located on bottom side 220 may be a closed loop with the interior of the loop configured to receive keel cutter 500 as depicted in FIG. 5. The closed nature of depth stopper 410 inhibits movement of keel cutter 500 out of bottom slot 222 away from bottom side 220. More specifically, the interior surface of the loop would retain the keel cutter in the interior of the loop if the keel cutter was to be displaced away from slot 22. Similarly, a keel holder 130 on upper side 120 is a closed loop which inhibits movement of keel cutter 500 away from slot 122 and upper surface 120. By inhibiting movement of keel cutter 500 away from tool 10, inadvertent damage to the patient, which could be caused by keel cutter 500 contacting unintended portions of the patient's anatomy, is minimized.

Figure 6:
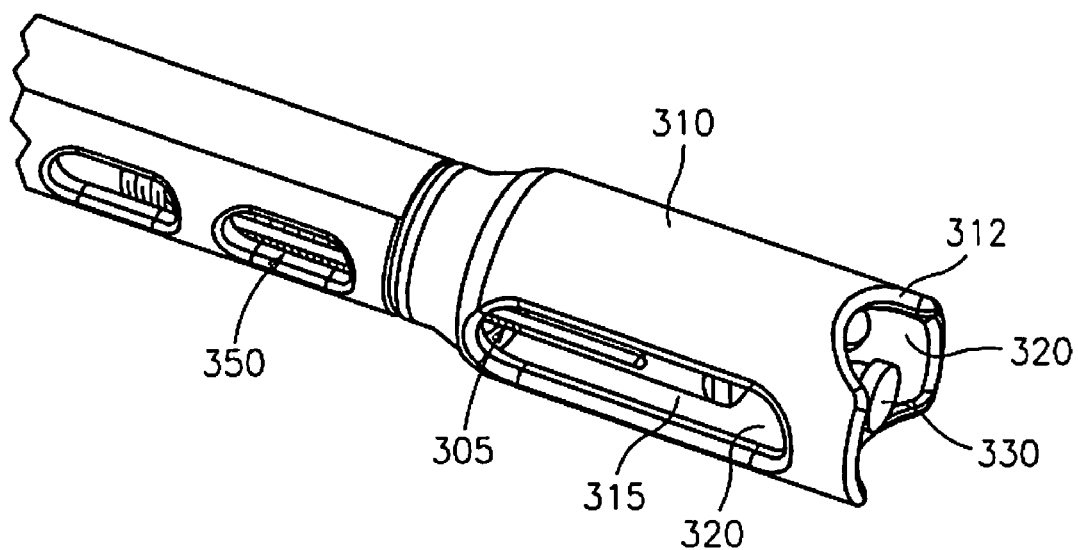
FIG. 6 is a perspective view of a proximal end of the handle assembly of the instrument of FIG. 1, in accordance with an aspect of the present invention.
Figure 7:
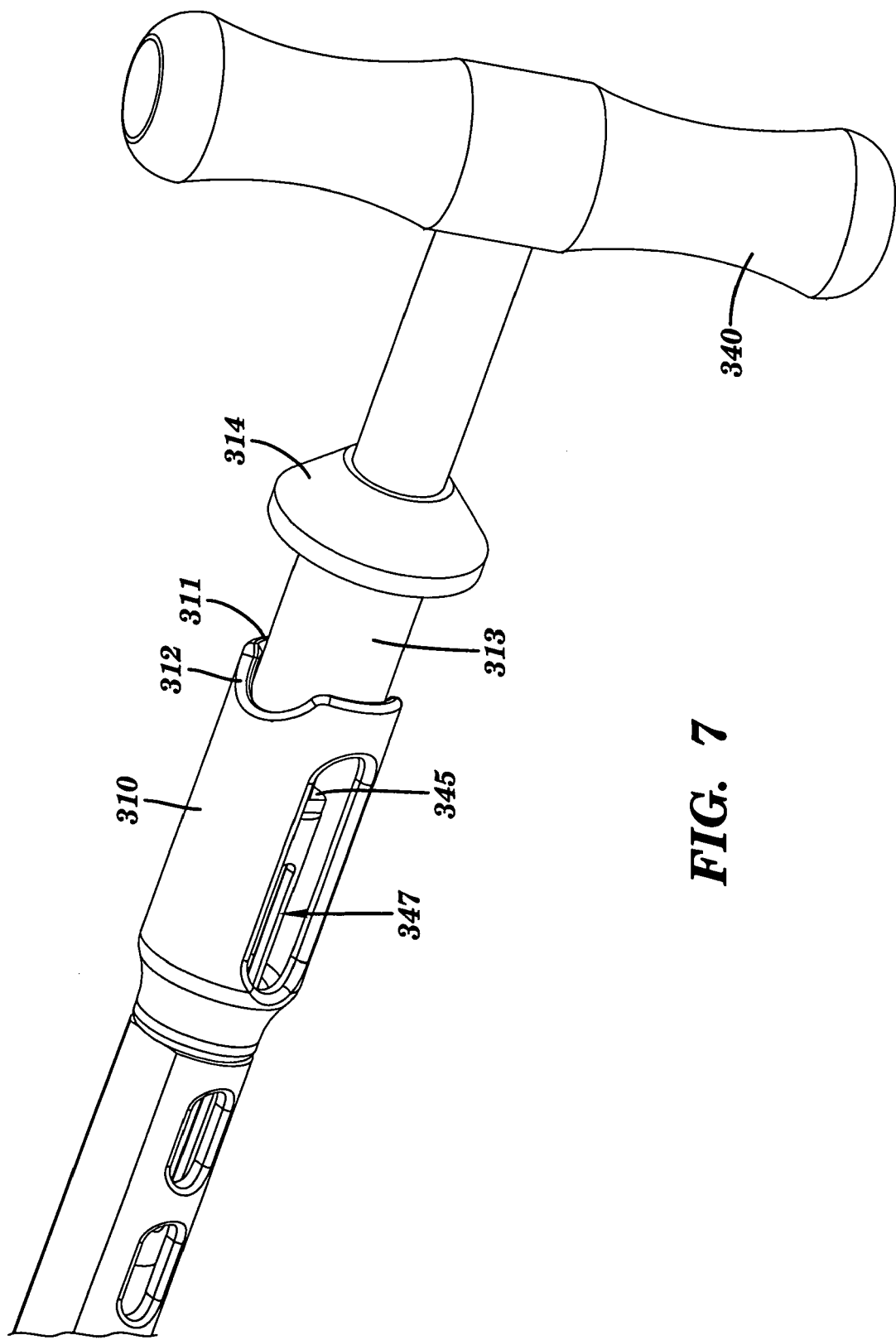
FIG. 7 is a perspective view of the proximal end of the handle assembly of FIG. 6 further including a releasable handle attached thereto, in accordance with an aspect of the present invention.

A proximal end 311 of handle assembly 300 includes a receiving flange 310 having a cavity 315 partially defined by a threaded interior radial surface 320 and having an impactable surface 330, as depicted in FIGS. 6-7. Receiving flange 310 is connectable to a suitable handle, such as a T-handle 340, which may be manipulated (e.g., rotated) by a user when connected to flange 310 to move arms 100 and 200, along with first and second contacting member 110 and 210, away from, and toward, one another. More specifically, an outer surface 345 of an end 347 of T-handle 340 may have threads configured to engage threaded interior radial surface 320 of the flange, which may include threads. Also, flange 310 may include a Hudson type connector or any other suitable structure for engagement with the T-handle.

For example, flange 310 may include one or more notches 312 at proximal end 311 of flange 310 configured (e.g., shaped and dimensioned) to receive finger tip(s) of the user. The notches allow the user to avoid having his finger(s) caught between proximal end 311 and another portion of T-handle 340 (e.g., a sleeve connecting portion 314) when an outer sleeve 313 moves toward flange 310 to attach T-handle 340 to flange 310 in the case of a Hudson type connection for example, as will be understood by those skilled in the art. Sleeve connecting portion 314 may connect outer sleeve 313 of T-handle 340 to an inner shaft (not shown) of T-handle 340. Outer sleeve 313 may be spring-loaded such that, when previously retracted relative to the shaft, outer sleeve 313 moves toward flange 310 when released by the user.

Expansion bar 350 may have threads 305 located at a proximal end thereof opposite front end 20 of tool 10. Threads 305 may engage with an inner threaded surface (not shown) of flange 310. Rotation of flange 310 itself or by T-handle 340 thus causes such movement of arms 100 and 200, along with first and second contacting members 110 and 210 via expansion bar 350. For example, flange 310 may be connected to an expansion bar 350, which may be driven forward by rotation of flange 310 by itself or flange 310 and T-handle 340. The movement of bar 350 forward may cause the arms and members to separate from one another as bar 350 contacts arms 100, 200 and/or first and second contacting members 110, 210 to distract the upper and lower vertebras to approximate heights or positions as described above. Movement of bar 350 away from front end 20 by flange 310 may cause or allow the arms and members to move from an expanded position to a collapsed position, for example.

Also, a distraction indicator is coupled to an actuating member such as expansion bar 350, which moves longitudinally therewith to provide an indication of the position of expansion bar 350 relative to first and second contacting members 110, 210 thereby providing an indication of a distance between the inner surfaces or outer surfaces of the members. For example, a distraction indicator, such as distraction height indicia 433 on expansion bar 350 viewable through a window 435 correspond to the distraction height of first and second contacting members 110 and 210 in the posterior end (i.e., front ends 117 and 217) thereof provided by the longitudinal positioning of expansion bar 350 therebetween. The measuring of the distance between the contacting members and thus the vertebra allow the user (e.g., the surgeon) to determine whether the space defined by the vertebra is of an appropriate size to begin the procedure for implanting a prosthetic in the spinal cavity. For example, if a measurement is taken revealing that the spinal cavity is not large enough, the contacting members may be further distracted via the T-handle and expansion bar until an appropriate space between the vertebra is created.

Further, when the T-handle is not attached to the flange, impactable surface 330 (e.g., a rigid head) may be accessed such that the user may impact the impactable surface 330 (e.g., with a hammer) to cause movement of tool 10 into the spinal cavity. More specifically, impactable surface 330 is coupled to first contacting member 110 and second contacting member 210. For example, impactable surface 330 may be connected to expansion bar 350 thereby connecting impactable surface 330, handle assembly, 300, arms 100 and 200, and first and second contacting members 110 and 210. Also, impactable surface 330 may be located entirely within receiving cavity 315. Further, impactable surface 330 may be located within a portion of T-handle 340 when T-handle 340 is received in cavity 315 and/or connected to flange 310. The location of impactable surface 330 within flange 310 allows a user to impact impactable surface 330 itself without the need for a cap to cover flange 310 to avoid damaging the flange. More particularly, instead of placing a cap over flange 310 to drive tool 10 into a spinal cavity, a user may directly impact impactable surface 330 which is located within cavity 315. The integral nature of impactable surface 330 avoids the necessity for a separate cap to protect flange 310 from damage to its internal threads or other portions thereof which may otherwise occur. Further, such integral nature prevents misplacement or loss of such a protective cap. Moreover, the location of impactable surface 330 within cavity 315 allows any impact to the remainder of flange 310 to be avoided due to its central interior location, i.e., away from other surfaces which could potentially by impacted and damaged.

Figure 3:
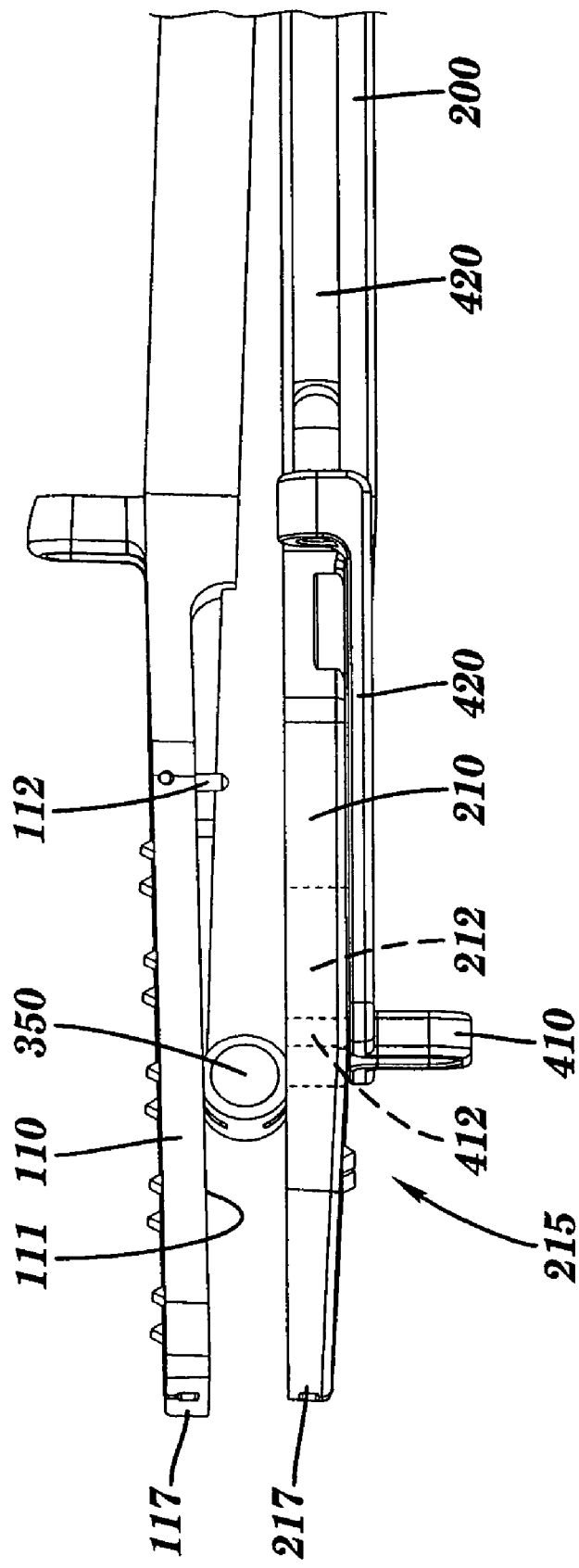
FIG. 3 is a side elevational view of a portion of the instrument of FIG. 1 showing a first contacting member and a second contacting member in an expanded configuration, in accordance with an aspect of the present invention.

The contacting members (e.g., first contacting member 110 and second contacting member 210) have radial interior surfaces (e.g., first radial interior surface 111) opposite each other, which may include aligning elements such as guide pins 112 located on such interior surface (e.g., interior surface 111) as depicted in FIGS. 2-3. Guide pins 112 may be radio opaque and may be aligned such that an imaginary line connecting them is substantially orthogonal to a longitudinal axis of the contacting members, arms (e.g., arms 100, 200) and/or tool 10. Also, guide pins 112 may be spaced equidistant from such a longitudinal axis of the arms, members and/or tool 10 as a whole. The guide pins may allow the alignment of tool 10 on a mid-line of a spine. More particularly, the guide pins may be aligned with one another (i.e., one behind the other) when viewed via a lateral x-ray image of the spinal cavity with tool 10 inserted therein. Such alignment may thereby locate a longitudinal axis of tool 10 or portions thereof (e.g., arms 100, 200 or first and second contacting members 110, 210) on a mid-line (not shown) of the spine (not shown). The guide pins may also be utilized to align tool 10 other than on the midline. For example, the tool may be aligned based on the position of the pins in a lateral x-ray, or the x-ray itself may be taken from a different direction.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A spinal disc replacement surgical instrument, comprising:
   a first contacting member disposed along a longitudinal axis and being positionable along an endplate of a first vertebra;
   a second contacting member disposed along the longitudinal axis and being positionable along an endplate of a second vertebra, the first vertebra and the second vertebra defining a spinal cavity, said second contacting member being movable relative to said first contacting member;
   a handle assembly coupled to said first and second contacting members;
   at least one actuating member positioned between said first contacting member and said second contacting member, said at least one actuating member being movable by said handle assembly from a first position, wherein said first and second contacting members include an unexpanded configuration relative to one another for insertion into the spinal cavity, to a second position providing an expanded configuration relative to one another, wherein said actuating member has an arcuate distal end portion configured to displace at least one of said first contacting member and said second contacting member away from each other to move said first contacting member and said second contacting member between the first position and the second position; and
   said first contacting member having a first distal end and said second contacting member having a second distal end, said first end having a first end shape configured to conform to a shape of the first vertebra and said second end having a second end shape configured to conform to a shape of the second vertebra, said first end shape and second end shape being different shapes,
   wherein the first contacting member includes elongated aligning elements being spaced apart and disposed in transverse alignment relative to the longitudinal axis, the aligning elements being configured for non-secured engagement with the actuating member such that the actuating member is disposed for relative slidable movement between the aligning elements.

2. The surgical instrument of claim 1, wherein said first contacting member and said second contacting member comprise different distal extents.

3. The surgical instrument of claim 1, wherein said first contacting member comprises a curved end shape and said second contacting member comprises a flat end shape.

4. The surgical instrument of claim 3, wherein said first contacting member comprises an inferior member and said second contacting member comprises a superior member.

5. The surgical instrument of claim 1, further comprising an adjustable depth regulator having a stop member configured to regulate a distance of said first end and said second end into said cavity defined by the first vertebra and the second vertebra, said stop member comprising a continuous loop configured to receive a keel cutter therein.

6. The surgical instrument of claim 5, wherein said depth regulator further comprises a control mechanism for regulating said stop member, said control mechanism being at least partially offset relative to a longitudinal axis of at least one of said handle assembly, said first member and said second member.

7. The surgical instrument of claim 6, wherein said control mechanism comprises a rotatable knob coupled to said stop member.

8. The surgical instrument of claim 6, wherein said stop member is connected to said control mechanism via a connecting member, said connecting member comprising a threaded portion received in said knob and configured to move in response to rotation of said knob.

9. The surgical instrument of claim 1, wherein said first contacting member is connected to said handle assembly by a first extending arm and said second contacting member is connected to said handle assembly by a second extending arm.

10. The surgical instrument of claim 9, wherein said first extending arm and said second extending arm are connected to each other at said handle assembly.

11. The surgical instrument of claim 1, wherein said first distal end is separated from said second distal end.

12. The surgical instrument of claim 1, wherein the aligning elements are radio opaque and disposed in a configuration to enable alignment of the surgical instrument relative to a body portion.

13. The surgical instrument of claim 12, wherein the aligning elements are guide pins.

14. A spinal disc replacement surgical instrument, comprising:
   a first contacting member disposed along a longitudinal axis and being positionable along an endplate of a first vertebra;
   a second contacting member disposed along the longitudinal axis and being positionable along an endplate of a second vertebra, the first vertebra and the second vertebra defining a spinal cavity, said second contacting member being movable relative to said first contacting member;
   said first contacting member connected to a handle assembly by a first extending arm and said second contacting member connected to said handle assembly by a second extending arm, the handle assembly including an actuating member having an arcuate distal end portion configured to expand the contacting members relative to one another; and
   an adjustable depth regulator extending from said handle assembly toward said first contacting member and said second contacting member, said adjustable depth regulator located at least partially longitudinally offset relative to at least one of said first arm and said second arm, said adjustable depth regulator comprising at least one stop member positionable in contact with one of the first vertebra and the second vertebra to limit an insertion depth of said first contacting member and said second contacting member in the spinal cavity,
   wherein the stop member is connected to at least one of the first contacting member and the second contacting member, and includes a loop portion that extends from the contacting member to define an inner surface configured to retain a cutting instrument in assembly with the surgical instrument,
   wherein the first contacting member includes opposing alignment pins being spaced apart and disposed in transverse alignment relative to the longitudinal axis, the pins being configured for non-secured engagement with the actuating member such that the actuating member is disposed for relative slidable movement and the contacting members are disposed for alignment with the spinal cavity.

15. The surgical instrument of claim 14, wherein said depth regulator comprises a depth regulator control mechanism coupled to said at least one stop member and configured to control movement of said at least one stop member, said depth regulator control mechanism located off-set relative to a longitudinal axis of said handle assembly.

16. The surgical instrument of claim 15, wherein said control mechanism comprises a rotatable knob coupled to said at least one stop member.

17. The surgical instrument of claim 16, wherein said at least one stop member is connected to said control mechanism via a connecting member, said connecting member comprising a threaded portion received in said knob and configured to move in response to a rotation of said knob.

18. The surgical instrument of claim 15, wherein said at least one stop member is connected to said controlling mechanism via a connecting member, said connecting member avoiding contact with at least one of said first arm and said second arm.

19. The surgical instrument of claim 15, wherein said at least one stop member comprises a closed loop configured to receive a keel cutter.

20. The surgical instrument of claim 15, wherein said depth regulator is at least partially spaced from said first arm and said second arm.

21. The surgical instrument of claim 14, wherein said depth regulator has a configuration longitudinally contoured to a configuration of at least one of the first contacting member and the second contacting member.

22. A spinal disc replacement surgical instrument, comprising:
  a first contacting member disposed along a longitudinal axis and being positionable along an endplate of a first vertebra;
  a second contacting member disposed along the longitudinal axis and being positionable along an endplate of a second vertebra, the first vertebra and the second vertebra defining a spinal cavity, said second contacting member being movable relative to said first contacting member and coupled to said first contacting member,
  said first contacting member and said second contacting member being movable between an unexpanded configuration relative to one another for insertion in the spinal cavity, and an expanded configuration relative to one another, wherein the first contacting member includes opposing guide pins being spaced apart and disposed in transverse alignment relative to the longitudinal axis;
  a handle assembly comprising a distal end coupled to said first contacting member and said second contacting member, the distal end of the handle assembly including an arcuate end portion configured for expanding the contacting members and being disposable between the guide pins, the pins being configured for non-secured engagement with the arcuate end portion such that the arcuate end portion is disposed for relative slidable movement and the contacting members are disposed for alignment with the spinal cavity;
  said handle assembly comprising a proximal end connectable to a releasable handle, said proximal end comprising a handle assembly cavity for receiving an end of said handle and said handle assembly cavity comprising an interior surface connectable to said handle;
  said handle assembly cavity comprising an impactable head configured to receive an impact and to transfer the impact to said handle assembly and to at least one of said first contacting member and said second contacting member; and
  an adjustable depth regulator extending from said handle assembly toward said first contacting member and said second contacting member, said adjustable depth regulator located at least partially longitudinally offset relative to said handle assembly, said adjustable depth regulator comprising at least one stop member positionable in contact with one of the first vertebra and the second vertebra to limit an insertion depth of said first contacting member and said second contacting member in the spinal cavity,
  wherein the stop member is connected to at least one of the first contacting member and the second contacting member, and includes a loop portion that extends from the contacting member to define an inner surface configured to retain a cutting instrument in assembly with the surgical instrument.

23. The surgical instrument of claim 22, further comprising a first arm connecting said first contacting member to said handle assembly and a second arm connecting said second contacting member to said handle assembly, and wherein said impactable head is coupled to said first arm and said second arm.

24. The system of claim 22 wherein said proximal end of said handle assembly further comprises a notch configured to receive a portion of a hand of user to avoid contact between the portion of the hand and a handle when the handle is connected to the handle assembly.

* * * * *